United States Patent
Grewe et al.

(10) Patent No.: US 10,471,056 B2
(45) Date of Patent: Nov. 12, 2019

(54) PHARMACEUTICAL FOR TREATING DIZZINESS HAVING DIFFERENT CAUSES

(71) Applicant: HENNIG ARZNEIMITTEL GMBH & CO. KG, Flörsheim am Main (DE)

(72) Inventors: Jan Christoph Grewe, Darmstadt (DE); Karl-Heinz Przyklenk, Gro.B-Gerau (DE)

(73) Assignee: HENNIG ARZNEIMITTEL GMBH & CO. KG, Florsheim am Main (DE)

( * ) Notice: Subject to any disclaimer, the term of this patent is extended or adjusted under 35 U.S.C. 154(b) by 0 days.

(21) Appl. No.: 15/322,092

(22) PCT Filed: Jun. 26, 2015

(86) PCT No.: PCT/EP2015/064560
§ 371 (c)(1),
(2) Date: Dec. 23, 2016

(87) PCT Pub. No.: WO2015/197833
PCT Pub. Date: Dec. 30, 2015

(65) Prior Publication Data
US 2017/0128441 A1    May 11, 2017

(30) Foreign Application Priority Data
Jun. 26, 2014 (EP) ..................................... 14174604

(51) Int. Cl.
 *A61K 31/495* (2006.01)
 *A61K 9/20* (2006.01)
 (Continued)

(52) U.S. Cl.
 CPC ............ *A61K 31/495* (2013.01); *A61K 9/209* (2013.01); *A61K 9/2054* (2013.01);
 (Continued)

(58) Field of Classification Search
 CPC .................................................... A61K 31/495
 See application file for complete search history.

(56) References Cited

U.S. PATENT DOCUMENTS 5,922,352 A * 7/1999 Chen .................... A61K 9/209
424/465
8,263,125 B2 * 9/2012 Vaya .................... A61K 9/2077
424/469

(Continued)

FOREIGN PATENT DOCUMENTS

| IN | 201102131 I3 * | 2/2013 | |
| WO | WO2006099864 A1 * | 9/2006 | ........... A61K 9/2013 |
| WO | WO 2014102253 A1 * | 7/2014 | ........... A61K 9/2013 |

*Primary Examiner* — Benjamin J Packard
(74) *Attorney, Agent, or Firm* — Graeser Associates International Inc; Dvorah Graeser

(57) ABSTRACT

The invention relates to a dosage form that is suitable for releasing an active ingredient over a long period of time. For this purpose, the active ingredient is released in two-stages in order to do away with an excessively frequent ingestion of the dosage form. The dosage forms according to the invention are for treating dizziness in humans. They are administered with or after a meal. The concept according to the invention provides that the pharmaceutical form has a dimensionally stable portion which, after ingestion of the dosage form by the patients, does not dissolve in the chyme-filled stomach for a number of hours. In this way, this dimensionally stable portion remains in the stomach until same is evacuated by the so-called "housekeeper waves". Another portion of the dosage form is formed in such a way that it dissolves within a short time of the patients ingesting same. In this way, a quick invasion of the active ingredient with corresponding plasma levels is ensured.

20 Claims, 2 Drawing Sheets

(51) Int. Cl.
*A61K 9/24* (2006.01)
*A61K 31/138* (2006.01)
*A61K 31/522* (2006.01)

(52) U.S. Cl.
CPC .......... *A61K 9/2059* (2013.01); *A61K 31/138* (2013.01); *A61K 31/522* (2013.01)

(56) References Cited

U.S. PATENT DOCUMENTS

2007/0196510 A1\* 8/2007 Gerber ................. A61K 31/401
 424/617
2011/0256218 A1\* 10/2011 Venkatesh ............ A61K 9/0056
 424/459

\* cited by examiner

PHARMACEUTICAL FOR TREATING DIZZINESS HAVING DIFFERENT CAUSES

The present invention relates to a dosage form that is suitable for releasing an active ingredient over a long period of time. For this purpose, the active ingredient is released in two stages, in order to do away with an excessively frequent ingestion of the dosage form. The dosage forms according to the invention are for treating dizziness in humans. They are administered with or after a meal. The concept according to the invention provides that the pharmaceutical form has a dimensionally stable portion which, after ingestion of the dosage form by the patient, does not dissolve in the chyme-filled stomach for a number of hours. In this way, this dimensionally stable portion remains in the stomach, until same is evacuated by the so-called "housekeeper waves". Another portion of the dosage form is formed in such a way that it dissolves within a short time of the patients ingesting same. In this way, a quick invasion of the active ingredient with corresponding plasma levels is ensured.

PRIOR ART

In prior art dosage forms for treating dizziness which are provided for the release of an active ingredient over a longer period of time are known. Till today however, a striking success for active ingredients which are suitable for the treatment of dizziness has not been achieved, especially in view of the complicated formulation of these active ingredients.

WO 2012/150246 A1 describes dosage forms for treating dizziness comprising several units containing active ingredient(s) with which a clocked release should be achieved. The units may be layers of a layered tablet, pellets, micro tablets or the same. Preferably, the units containing active ingredient(s) have small diameters of only few millimeters. In this way, a better solubility in the intestine should be achieved, because the units containing active ingredient(s) are characterized by a large surface area. The dosage form should simulate an administration of the active ingredient several times a day. For this purpose, it comprises a portion which is quickly dissolved in the stomach and a slowly soluble portion. But for the functioning of this dosage form a low pH value in the stomach is necessary. This can also be seen in the examples of the dosage forms, because their decomposition has been determined in 0.1 N HCl. But after a meal the pH value in the stomach is increased. So this document does not suggest an administration after a meal. In addition, after the ingestion the units are not suitable for remaining in the stomach, because they have a small diameter. Thus, they can pass the pylorus sphincter. Therefore, the dosage forms described in this prior art document are not suitable for guaranteeing a prolonged release of the active ingredient as well as also a corresponding initial dose of the active ingredient. The design of the different compartments in the dosage form results in the fact that the single particulate units are relatively quickly transported from the stomach into the intestine. Then, the units containing active ingredient(s) are transported through the intestine and they relatively soon leave the areas of the gastrointestinal tract in which the active ingredient can be resorbed. Normally, in lower sections of the intestine the active ingredient is resorbed worse and there also its dissolution from the dosage form is worse, because the amount of available liquid is strongly limited. In particularly this is the case, when the dosage form is not ingested with or after a meal and when the dosage form is designed such that it leaves the stomach already a short time after its ingestion. On the contrary, the dosage forms according to the present invention are designed such that at least the dimensionally stable portion remains in the stomach of the patient and is maintained there at least so long as a minimum amount of chyme is present in the stomach. Normally, the housekeeper waves only start, when a large part of the chyme has already been transported into the small intestine. The dosage form according to the present invention with its concept of comprising a dimensionally stable portion utilizes the fact that the stomach retains a portion of the chyme and does not allow particulate constituents having a diameter of more than 2 mm to pass through the pylorus sphincter.

WO 2012/175737 A1 relates to an active ingredient matrix and to a dosage form containing this matrix. The mixing of the active ingredient with the chyme after a meal is discussed. The matrix should allow a continuous release during the passage through the gastrointestinal tract. It is mentioned that the active ingredient may be transported with the chyme. The residence time in the stomach should be increased. A coat-core tablet is mentioned. A dosage form comprising two portions of active ingredient(s), one portion within and one portion outside the matrix, is described. In this case, the matrix may comprise a coating. Obviously, a release in three stages should be achieved. But in this prior art document it is also described that the respective dosage form should already release a large part of the active ingredient in the stomach. The release should be facilitated from a matrix which is a constituent of the dosage form. It is described to be particularly important that the active ingredient matrix is very quickly dissolved in the gastrointestinal tract. Obviously, a dimensionally stable portion is not proposed. Thus, the galenic design of the dosage form described in this prior art document is absolutely different from the design according to the present invention. According to the present invention, a certain portion of the dosage form is not dissolved in the stomach, but retains its structural integrity. Thus, the active ingredient being contained in this portion of the dosage form will not be dissolved and will not be mixed with the chyme. An embodiment in which the dosage form comprises two portions of active ingredient(s) releasing the active ingredient at different sites is described, but obviously this part of the disclosure relates to coated pellets or tablets.

WO 2013/030119 A1 describes presentation forms with stabilized particles of active ingredient(s). The dissolution rate of the active ingredient cinnarizine should be improved. The presentation form is a retard dosage form. A dosage schedule is not proposed.

WO 2012/175747 A1 relates to a method for the preparation of a dosage form comprising several subunits. This may also mean coat-core tablets. The ingestion after a meal is mentioned. Ingestions several times a day are not necessary. The dosage form described in this prior art document should be particularly advantageous in connection with pellets and micro tablets which on their part have already such a small diameter that they can easily enter from the stomach into the intestine. Thus, the concept of this disclosure is totally different from that of the present invention.

WO 2014/001268 A1 relates to a dosage form for prolonged release. The dosage form comprises several compartments, such as for example a layered tablet. The problems in connection with the ingestion after a meal are discussed. It is hypothesized that the initial pH value in the stomach is only again achieved after a period of time of up to 90 minutes. The dosage forms are characterized by a long residence time in the stomach. The layered tablet may be a coat-core tablet. Also a dosage form with long residence time in the stomach is described. A nearly linear release is intended. The dosage form described in this prior art document is substantially different from the dosage forms according to the present invention due to the fact that an administration with or after the meals has not been identified as advantageous and that not both different compartments of the dosage form which are present therein (layered tablet, coat-core tablet) contain a proportion of the active ingredient. So an initial dosage of the active ingredient cannot be provided, in contrast to the disclosure according to the present invention.

OBJECT OF THE INVENTION

With the prior art dosage forms till today it was not possible to achieve a plasma level of the active ingredient in patients which provides a satisfactory duration of action and at the same time a satisfactory prevention of plasma levels which are too high and which guarantees an acceptably early onset of action after ingestion.

Therefore, it is the object of the present invention to provide a dosage form which allows an administration of an active ingredient in such a manner that an administration of more than two times a day is not necessary, that plasma levels which are too high are prevented and that an early onset of action is guaranteed.

Solution

This object is solved by the subject matter of the patent claims.

The dosage form according to the present invention comprises
- an active ingredient or a derivative, salt and/or prodrug thereof,
- a dimensionally stable portion which does not dissolve in an aqueous medium at a pH value of <5 during a period of time of 2 hours also under stirring and which does not erode under this conditions in an extent that its smallest diameter decreases to a value of smaller than 5 mm, preferably smaller than 4 mm and particularly preferably smaller than 2 mm,
- a portion which is soluble in gastric juice which dissolves in an aqueous medium at a pH value of <5 during a period of time of shorter than 2 hours or which erodes under this conditions in an extent that its largest diameter decreases to a value of <2 mm.

Preferably, the aqueous medium is the phosphate buffer solution pH 4.5 R according to the European Pharmacopoeia (Ph. Eur. 7.0). A suitable testing apparatus is the apparatus for the determination of the disintegration time of tablets according to the European Pharmacopoeia (Ph. Eur. 7.0, chapter 2.9.1). Optionally, it is stirred with a paddle stirrer apparatus according to the European Pharmacopoeia (Ph. Eur. 7.0, chapter 2.9.3).

Both, the dimensionally stable portion and also the portion which is soluble in gastric juice contain a partial amount of the active ingredient. The dosage form is intended for the use in a method for treating dizziness in humans comprising administering the dosage form to a patient with or after a meal at most two times a day. Preferably, the administration is conducted within a time frame of up to 1 hour after the ingestion of a meal.

Thus, the dosage form according to the present invention releases from the portion which is soluble in gastric juice a part of the amount of the active ingredient already a short time after the ingestion by the patient. In this way, an initial dose of the active ingredient is released immediately after the ingestion. Since the dosage form should be ingested with or after a meal, the pH value in the stomach is increased, due to the fact that the gastric acid is diluted with the chyme. Therefore, it is necessary that the portion of the dosage form which is soluble in gastric juice already dissolves and/or erodes at a pH value of lower than 5. Gradually, the chyme enters the small intestine through the pylorus sphincter. There the active ingredient is resorbed and this results in a corresponding plasma level of the active ingredient so that its effect can arise.

The dimensionally stable portion of the dosage form is characterized by the fact that it is not immediately dissolved and/or eroded under the given conditions, when it is ingested with or after a meal. Rather, the dimensionally stable portion retains a size which prevents a transport of it into the small intestine through the pylorus sphincter. For that it is intended according to the present invention that the dimensionally stable portion also after a residence time of 2 hours in the stomach at a pH value of lower than 5 is not dissolved or eroded in such an extent that its smallest diameter has a value of lower than 2 mm. So it can be achieved that the dimensionally stable portion remains in the stomach, until the chyme has substantially completely entered into the small intestine. When this is the case, the stomach forwards those food components which are still present in the stomach into the small intestine by so-called "housekeeper waves".

Now, the dimensionally stable portion further releases active ingredient in the small intestine so that it can be resorbed. So it is achieved that furthermore a sufficiently high plasma level of the active ingredient is provided.

According to the present invention it is preferable that the dimensionally stable portion of the dosage form is designed such that the active ingredient is released from the dimensionally stable portion over a prolonged period of time. For this purpose, the dimensionally stable portion preferably comprises at least one emulsifier.

The meal with and/or after which the dosage form is ingested, with respect to its composition is preferably characterized by the following properties:
carbohydrates: >50 g
fat: >10 g
protein: >10 g The proportion of the active ingredient in the portion which is soluble in gastric juice preferably corresponds to about 1% to 70%, further preferably 5 to 40%, more preferably 8% to 15% of the amount of active ingredient in the dimensionally stable portion. In one embodiment this proportion is 20% to 65% of the amount of active ingredient in the dimensionally stable portion. Preferably, the dosage form according to the present invention is free from antioxidants and/or complexing agents.

Active Ingredient

Basically, the active ingredient in the dosage form according to the present invention can be selected in an arbitrary manner. But the dosage form according to the present invention is designed such that an active ingredient which under normal conditions is only poorly dissolved in the pH range of the small intestine can correspondingly be released. Preferably, the active ingredient is characterized in an aqueous solution at a pH value of 7 and at a temperature of 22° C. by a solubility of lower than 0.01 mg/ml. Thus preferably, the active ingredient has low solubility, it is "virtually insoluble" according to the solubility classification of the European Pharmacopoeia (Ph. Eur. 7, 2011). Preferably, the solubility at a pH value of 7 and at 22° C. in an aqueous solution is at most 0.005 mg/ml, further preferably at most 0.001 mg/ml and still more preferably even lower than 0.001 mg/ml.

Solubility means the concentration of the dissolved substance in a saturated solution at a certain temperature. According to the present invention, the solubility of the active ingredient relates to the solubility in an aqueous solution at a temperature of 22° C. under normal pressure. This information about the temperature as well as the whole information about the temperatures given below comprise, according to the present invention, preferably the concretely given value, including a range of ±3° C. around the given temperature value. Unless otherwise stated, the information about the solubilities given below relates to the solubility under normal pressure. The measurement is conducted in the standard and/or buffer solutions of the European Pharmacopoeia (Ph. Eur. 7) having the respective pH value.

The aqueous solution for achieving a pH value of 7 comprises a phosphate buffer and water. The composition can be found in the European Pharmacopoeia (Ph. Eur. 7; phosphate buffer solution pH 7.0 R). The measurement of the pH value is carried out with methods which are known by a person skilled in the art, for example by means of a commercially available pH meter.

For the determination of the solubility, methods which are known by a person skilled in the art are used, such as for example the sediment method, the temperature method or the distribution method. In particularly suitable is the distribution method in which the active ingredient is dissolved in a second solvent which is immiscible with the respective aqueous solution for which the solubility of the active ingredient should be determined. Both liquids are intensively shaken until the equilibrium is established and then they are separated from each other.

Preferably, the active ingredient is selected from the BCS class II or BCS class IV, wherein it is particularly preferable, when the active ingredient is an active ingredient of the BCS class II. Especially such active ingredients profit from the dosage forms according to the present invention in an exceptionally positive manner, since the dissolution of the active ingredient in the small intestine is especially promoted.

Preferably, the active ingredient has at least one basic functional group. Till today, especially such functional groups which are normally connected with pH dependent solubility cause considerable difficulties in the formulation of dosage forms with prolonged release.

A group is in particular a basic group, when it can acquire protons (Brønsted base). In the sense of the present invention only groups having a $pK_B$ value of at most 9, further preferably a $pK_B$ value of at most 8.5 and more preferably a $pK_B$ value of at most 8 are considered as basic functional groups.

The basic functional group is preferably selected from aliphatic nitrogen-containing groups or a nitrogen-containing heterocycle. In the sense of the present invention the term "nitrogen-containing heterocycle" means nitrogen-containing groups which are a constituent of aromatic hydrocarbons. Besides the nitrogen-containing group the aromatic hydrocarbons may still comprise further heteroatoms as ring members. But preferable "nitrogen-containing heterocycles" are such ones which besides nitrogen only contain carbon atoms as ring members. Aliphatic nitrogen-containing groups are preferably selected from amino groups and guanidine groups. The term "amino group" comprises primary, secondary and tertiary amino groups. Also nitrogen atoms in saturated or partially unsaturated cyclic hydrocarbons which besides the nitrogen atom may still comprise further heteroatoms, including further nitrogen atoms as ring members are an amino group.

It is particularly preferable, when the basic functional group is selected from amino group, guanidine group and nitrogen-containing heterocycle. It is still more preferable, when the basic functional group is an amino group. Such active ingredients especially profit from the dosage forms according to the present invention due to their distinctly pH dependent solubility.

Especially active ingredients which are polybasic, thus contain at least two basic functional groups, profit from the dosage form according to the present invention in a particular manner. Particularly preferably, therefore, the active ingredient contains at least two basic functional groups, still more preferably exactly two basic functional groups. It is still more preferable, when the active ingredient comprises two amino groups.

So, normally, the active ingredient is protonated, when it comes into contact with gastric juice, and thus water-soluble in this acidic milieu. But in the intestine at higher pH values of 6 and more, the active ingredient can only poorly be dissolved. This is in particularly the case, when the active ingredient does not comprise acidic functional groups.

Thus it is further preferable, when the active ingredient does not comprise acidic functional groups. Acidic functional groups are such ones which in the uncharged condition of the active ingredient are capable of donating protons. In particularly, the active ingredient has no acidic groups having a $pK_A$ value of lower than 5. Acidic groups in particularly comprise carboxyl groups, sulfur-containing acid groups such as sulfonic acid groups and sulfuric acid esters, phosphorus-containing acid groups, hydroxyl groups including phenolic hydroxyl groups and amide groups. In particularly, no carboxyl groups and/or hydroxyl groups are contained in the active ingredient. Thus it is particularly preferable, when the solubility of the active ingredient is substantially characterized by the basic functional group, preferably selected from amino group, guanidine group and nitrogen-containing heterocycle, especially preferably by the at least one amino group. In any case, such active ingredients particularly profit from the design of the dosage form according to the present invention.

Preferably, at pH values of <7 and at a temperature of 22° C. the active ingredient has higher solubility than at a pH value of 7 and at 22° C. Preferably, at a pH value of 1 and at 22° C. the active ingredient shows in an aqueous solution a solubility of higher than 0.1 mg/ml, further preferably at least 0.5 mg/ml, further preferably at least 1 mg/ml, still further preferably at least 1.3 mg/ml and particularly preferably at least 1.5 mg/ml. Thus, at a pH value of 1 the active ingredient is preferably at least "very poorly soluble", further preferably at least "poorly soluble" according to the solubility classification of the European Pharmacopoeia (Ph. Eur. 7). At pH values of higher than 7, preferably, the solubility of the active ingredient is at most 0.01 mg/ml, further preferably at most 0.001 mg/ml. For example, at a pH value of 9 and at 22° C. in an aqueous solution the solubility of the active ingredient is preferably at most 0.01 mg/ml and more preferably at most 0.001 mg/ml.

As an aqueous solution for achieving a pH value of 1 the standard solution of hydrochloride acid according to the European Pharmacopoeia (Ph. Eur. 7) consisting of hydrochloride acid and water, which means a 0.1 N (0.1 mol/l) hydrochloride acid solution, is used. For the determination of the solubility of the active ingredient at a pH value of 9 the phosphate buffer solution pH 9.0 R is suitable.

Preferably, the active ingredient used according to the present invention has an n-octanol/water distribution coefficient (log $P_{OW}$) at 20° C. of higher than 1, preferably higher than 2, more preferably higher than 3 and particularly preferably higher than 4, in particularly higher than 5. This distribution coefficient is a measure for the lipophilicity of a substance. As already mentioned above, especially lipophilic active ingredients profit from the dosage form of this invention. The advantage for such active ingredients is also very distinct, because normally the resorption of lipophilic active ingredients functions very well as soon as these substances are dissolved. In other words, the dissolution of these active ingredients from a dosage form is the step which determines the rate of the uptake of the active ingredient into the body.

Nevertheless, there are also active ingredients having a lipophilicity which is so distinct that the formulation proposed here is not sufficient for guaranteeing sufficient bioavailability. Therefore, the active ingredient has an n-octanol/water distribution coefficient (log $P_{OW}$) at a temperature of 20° C. of preferably at most 100, further preferably at most 50, in particularly preferably at most 30, particularly preferably at most 15 and in particularly at most 7.

For further improving the solubility of the active ingredient after application, it is preferable according to the present invention to use the first active ingredient in small particle size. Therefore, the first active ingredient in the dosage form of this invention has preferably a mean particle size of at most 1000 nm, further preferably at most 600 nm and particularly preferably at most 300 nm. According to the present invention, the mean particle size is preferably measured by the analysis method of dynamic light scattering. The small particle size is of particular importance, when the active ingredient cannot or only hardly be dissolved in the emulsifier. This is often the case, when the emulsifier comprises a particularly large hydrophilic portion, such as for example at lot of poloxamers, and/or when the active ingredient is extremely lipophilic.

According to the present invention it is preferable, when the active ingredient can be dissolved in the emulsifier nearly completely, particularly preferably completely. In this way, an improved release can be achieved. This effect can be achieved by the measure that the lipophilic portion of the emulsifier is adjusted to the lipophilicity of the active ingredient. How this can be achieved, follows from the statements about the emulsifier and its molecular structure below. Thus it is particularly preferable, when the active ingredient is completely dissolved in the dosage form according to the present invention.

In particularly active ingredients which in the case of immediately releasing dosage forms have to be administered at least three times a day, profit from the dosage form according to the present invention. Thus, the active ingredient is preferably an active ingredient which in the case of ingestion of immediately releasing dosage forms has to be administered at least three times a day.

It is particularly preferable, when the active ingredient is selected from active ingredients of the active ingredient classes antihistamines, antiemetics, antivertiginous drugs and/or calcium channel blockers. In a particularly preferable embodiment the active ingredient is cinnarizine, a cinnarizine salt and/or a cinnarizine derivative, in particularly a prodrug. It is especially preferable, when the first active ingredient is cinnarizine.

The proportion of the active ingredient in the dosage form is preferably at least 1% by weight, further preferably at least 2% by weight, more preferably at least 3% by weight and particularly preferably at least 5% by weight or at least 10% by weight, based on the total mass of the dosage form according to the present invention. A certain proportion of the active ingredient is necessary for achieving the desired pharmacological effect. But the proportion of the active ingredient should not be too high, because the improvement of the dissolution of the active ingredient cannot be achieved with sufficient certainty for arbitrarily high proportions of active ingredient. Therefore in preferable embodiments, the content of active ingredient of the active ingredient in the dosage form is limited to at most 25% by weight, further preferably at most 18% by weight, more preferably at most 15% by weight and particularly preferably at most 12% by weight, based on the total mass of the dosage form according to the present invention.

Preferably, the active ingredient is used in the dosage form according to the present invention in an amount of at least 20 mg or particularly preferably at least 30 mg. Preferably, the amount of the first active ingredient in the dosage form according to the present invention should not exceed a value of 100 mg and particularly preferably 80 mg.

The partial amount of the active ingredient in the portion of the dosage form which is soluble in gastric juice is preferably smaller than the partial amount of the active ingredient in the dimensionally stable portion. The partial amount of the active ingredient in the dimensionally stable portion is preferably between 55 and 99%, further preferably between 70 and 95% and more preferably between 80 and 93% of the total amount of active ingredient of this active ingredient in the dosage form. In preferable embodiments this proportion is 55 and 75% of the total amount of active ingredient in the dosage form, particularly preferably between 60 and 70%. Then preferably, the residual amount is present in the portion which is soluble in gastric juice.

Emulsifier

The emulsifier in the dimensionally stable portion has a dual function. This dual function consists on the one hand in the provision of the release of the active ingredient distributed over a longer period of time and on the other hand in the support of the solubility of the active ingredient, in other words: in controlling the release of the active ingredient.

Intensive tests have shown that this dual function within the context of the dosage form according to the present invention can be provided particularly well by the emulsifier described below. Preferably, the portion of the dosage form which is soluble in gastric juice contains no emulsifier, since the function of the portion which is soluble in gastric juice is a release of the active ingredient which is as quick as possible, in the sense of an initial dose.

For the purpose that the improvement of the dissolution and the modification of the release of the proportion of the active ingredient is provided particularly well, the emulsifier should preferably be characterized by an HLB value of at least 1 and at most 16, in particularly at least 9 and at most 14. Preferably, the emulsifier is not an ionic one.

It has been shown that emulsifiers having a certain structural motif achieve particularly advantageous results. This structural motif is a polyethylene glycol chain. It was found that emulsifiers having this structural motif, thus with at least one polyethylene glycol chain, fulfill the dual function which is desired according to the present invention. On the one hand, at high pH values, starting at about pH 4, they result in an improvement of the solubility of the first active ingredient. On the other hand, especially in the case of low pH values, namely then, when the active ingredient is preferably characterized by higher solubility, they result in a retardation of the release. According to the present invention, this is a desired behavior, because the release of the active ingredient from the dimensionally stable portion should be realized over a long period of time in an as continuous as possible manner.

The polyethylene glycol chain is the hydrophilic part of the emulsifier and it is connected with a lipophilic part. Advantageously, the lipophilic part can be a glyceride residue or another polyalkylene oxide chain. A further advantage of the polyethylene glycol chain is that it easily can be chemically modified, thus lengthened or shortened. In this way, the hydrophilic part can be adjusted to the active ingredient.

As glyceride residues mono- and diglyceride residues can be used, wherein diglyceride residues are preferable. In some circumstances, the lipophilicity of monoglyceride residues, depending on the chain length of the involved fatty acid residues, may not be high enough.

As polyalkylene oxide chains in particularly polyalkylene oxides comprising non-interrupted carbon chains of at least 3 carbon atoms can be used. A preferable example for a polyalkylene oxide chain in the emulsifier of this invention is polypropylene oxide.

These emulsifiers can be obtained by methods which are known by a person skilled in the art. For example, polyethylene glycol glycerides can be prepared by reaction of the corresponding glycerides with polyethylene glycol. Commercially available polyethylene glycol glycerides are, for example, Gelucire® 43/01 and Gelucire® 50/13.

In other words: the emulsifiers which can be used in the dosage form according to the present invention comprise the following structural element:

$$R^1-O-[CH_2-CH_2-O]_n-R^2 \quad \text{(formula I)},$$

wherein $R^1$ and $R^2$ are the same or different, and wherein $R^1$ and $R^2$ independently from each other are hydrogen, alkyl, glyceride or polyalkylene oxide. Preferably, alkyl is a short-chain alkyl, i.e. it has a chain length of at most 6 carbon atoms. Preferably, $R^1$ and $R^2$ independently from each other are hydrogen, glyceride or polyalkylene oxide.

When one residue $R^1$ or $R^2$ is hydrogen, then the residues $R^1$ and $R^2$ are different, i.e. the other residue each is not hydrogen; and when $R^1$ or $R^2$ is alkyl, then the residues $R^1$ and $R^2$ are different, i.e. the other residue each is not alkyl. Otherwise the molecule would not have the required emulsifying effect. Preferably, $R^1$ and $R^2$ are neither hydrogen nor alkyl, when the other residue each is hydrogen or alkyl.

n is the number of the chain members in the polyethylene oxide chain. n is an integer of at least 4, preferably at least 10 and particularly preferably at least 20. When n is smaller, then the effect desired according to the present invention is not so distinct, because the lipophilic part of the emulsifier is too small. In preferable embodiments n is not higher than 100, in particularly not higher than 50, further preferably not higher than 40 or not higher than 30. It has been shown that longer chains result in slower degradation of the emulsifier by pancreatin and lipases. In this way, the prolonged release can be controlled. But when the chain is too long, then the release of the active ingredient from the dosage form is not quick enough.

When $R^1$ and/or $R^2$ are a polyalkylene oxide residue, then the residue has the following general formula:

$$-O-[Y-O]_m-R^3 \quad \text{(formula II)},$$

wherein $R^3$ is hydrogen or alkyl, in particular a short-chain alkyl (up to $C_6$). Y is an alkylene group having a carbon chain length of at least $C_3$ and preferably at most $C_6$, further preferably at most $C_4$.

m is the number of the chain members in the polyalkylene oxide chain. m is preferably an integer of at least 3, in particularly at least 5 and particularly preferably at least 10. Preferably, m should not exceed an integer of 50, in particularly 40 and particularly preferably 30 or 20. In preferable embodiments $R^1$ and $R^2$ are polyalkylene oxide residues.

When $R^1$ and/or $R^2$ are glyceride residues, then the glyceride residue has the following general formula:

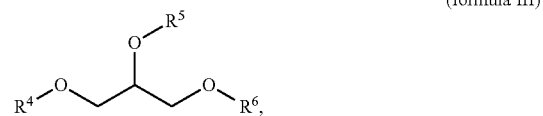

(formula III)

wherein formula III at one of the sites $R^4$, $R^5$ or $R^6$ is connected with the structural element of formula I. According to the present invention it is not of interest at what site the structure of formula III is connected with the structure of formula I. Thus, one of the residues $R^4$, $R^5$ or $R^6$ has the structure of formula I. Then, for both remaining residues the following is true:

$R^4$ is preferably hydrogen or a fatty acid residue. The fatty acid residue $R^4$ has preferably a chain length of at least $C_6$, further preferably at least $C_8$ and particularly preferably at least $C_{10}$. A minimum chain length should not fall below a certain value, so that the glyceride residue is sufficiently lipophilic. The number of the carbon atoms in the fatty acids is preferably even-numbered. The chain length should preferably not exceed a value of $C_{22}$, further preferably $C_{18}$ and particularly preferably $C_{16}$, since otherwise the solubility of the emulsifier may become compromised.

$R^5$ is preferably hydrogen or a fatty acid residue. The fatty acid residue $R^5$ has preferably a chain length of at least $C_6$, further preferably at least $C_8$ and particularly preferably at least $C_{10}$. A minimum chain length should not fall below a certain value, so that the glyceride residue is sufficiently lipophilic. The number of the carbon atoms in the fatty acids is preferably even-numbered. The chain length should preferably not exceed a value of $C_{22}$, further preferably $C_{18}$ and particularly preferably $C_{16}$, since otherwise the solubility of the emulsifier may become compromised.

$R^6$ is preferably hydrogen or a fatty acid residue. The fatty acid residue $R^6$ has preferably a chain length of at least $C_6$, further preferably at least $C_8$ and particularly preferably at least $C_{10}$. A minimum chain length should not fall below a certain value, so that the glyceride residue is sufficiently lipophilic. The number of the carbon atoms in the fatty acids is preferably even-numbered. The chain length should preferably not exceed a value of $C_{22}$, further preferably $C_{18}$ and particularly preferably $C_{16}$, since otherwise the solubility of the emulsifier may become compromised.

Preferably, two of the residues $R^4$, $R^5$ and $R^6$ are fatty acid residues. Correspondingly, then this is a diglyceride group.

It has to be noted that the correct chain length of the fatty acid residues strongly correlates with the number of the chain members in the polyethylene oxide chain (n). When the polyethylene oxide chain is longer, then also the fatty acid chains may be longer.

The emulsifiers described herein can be produced by reaction of corresponding mono-, di- and/or triglycerides with respective polyalkylene oxides. These educts are commercially available. The emulsifiers according to the present invention are preferably mixtures of the mentioned substances.

In preferable embodiments the emulsifier is selected from Gelucire® 50/13, Gelucire® 43/01, Poloxamer 407 and mixtures thereof, wherein Gelucire® 50/13 is particularly preferable.

A good solubilizing effect is achieved, when the ratio of the masses of active ingredient to emulsifier in the dimensionally stable portion is at least 1 to 30, further preferably at least 1 to 20 and particularly preferably at least 1 to 10 and further preferably at least 1 to 6. The mentioned ratio is preferably at most 1 to 1, further preferably at most 1 to 2 and particularly preferably at most 1 to 3. As a general rule it is true that a larger amount of emulsifier facilitates a better solubilizing effect. But it has to be considered that a dosage form should not exceed a certain maximum volume, so that the ingestion thereof does not unnecessarily become unpleasant. In addition, an amount of emulsifier which is too high may also result in restraint of the dissolution and/or the release of the active ingredient.

The dimensionally stable portion of the dosage form preferably contains the emulsifier in a proportion of at least 15% by weight, further preferably at least 20% by weight, still further preferably at least 22% by weight and particularly preferably at least 25% by weight, based on the total mass of the dimensionally stable portion. The proportion of the emulsifier should preferably not exceed a value of 50% by weight, further preferably 40% by weight and particularly preferably 35% by weight, based on the total mass of the dimensionally stable portion. In a test for determining the optimum ratio of the solubilizing effect and the volume of the dosage form, these amounts have shown to be particularly advantageous. The mass proportion of the emulsifier in the dosage form is preferably at least 4% by weight, further preferably at least 10% by weight and particularly preferably at least 15% by weight, but preferably at most 40% by weight, further preferably at most 30% by weight and particularly preferably at most 25% by weight.

In particularly preferable embodiments instead of the emulsifiers mentioned above or in addition to the emulsifiers mentioned above at least one phospholipid is used. Preferably, the phospholipid is selected from phosphatidylcholines (lecithins), phosphatidylethanolamines (cephalins), phosphatidylserines, sphingomyelins and mixtures thereof. Particularly preferably are phosphatidylcholines (lecithins) Surprisingly it was found that phospholipids also result in the same above described advantageous effects as the emulsifiers mentioned above, and that they act together with them in a synergistic manner.

Thus, the emulsifier may be a phospholipid. Preferably, the emulsifier comprises the phospholipid in addition to at least one of the emulsifiers mentioned above. In this way, the phospholipid intensifies the advantageous effects of the above mentioned substances.

Pharmacokinetic and Dosing

As already described at the beginning, with the dosage form according to the present invention an advantageous pharmacokinetic which is characterized by a quick onset of the effect and a long duration of the effect should be achieved. It is preferable, when with the use of the dosage form according to the present invention a pharmacokinetic can be achieved which is characterized by a $C_{max}$ at the latest 8 hours after the ingestion. It is according to the present invention that in the treatment of dizziness in humans a preferably permanent effect is achieved which primarily during the day is of particular importance. Thus it is particularly preferable, when an ingestion of the dosage form with or after breakfast is intended.

The dosage form of this invention is suitable for providing a level of the active ingredient which corresponds to an effective concentration of the active ingredient over a period of time of at least 16 hours, further preferably at least 18 hours and particularly preferably at least 20 hours.

The dosage form according to the present invention is administered less than three times a day, preferably two times a day and particularly preferably only one time a day. The group of patients for which the dosage form is intended is preferably selected from patients being older than 40 years, further preferably older than 50 years and particularly preferably older than 60 years. For this age group the treatment of dizziness is of particular importance.

In particularly, the dosage form may be designed as a layered tablet, wherein the dimensionally stable portion and the portion which is soluble in gastric juice each represent one layer, or as a coat-core tablet, wherein the dimensionally stable portion represents the core and the portion which is soluble in gastric juice represents the coat, wherein between the core and the coat an enteric film may be arranged.

Further Adjuvants

For guaranteeing the properties of the dosage form which are desired according to the present invention adjuvants are used. One adjuvant is the emulsifier which has already been discussed above. Besides the emulsifier the dimensionally stable portion of the dosage form preferably also comprises at least one structural agent and/or at least one disintegrating agent. Also the portion of the dosage form which is soluble in gastric juice preferably contains a structural agent and/or a disintegrating agent. In particularly preferable embodiments the proportion by mass of the disintegrating agent in the dimensionally stable portion is lower than that one in the portion which is soluble in gastric juice. The disintegrating agent promotes the decomposition of the dosage form and thus supports the release of the active ingredient. In preferable embodiments the dimensionally stable portion and the portion which is soluble in gastric juice contain different structural agents and/or different disintegrating agents.

Structural Agents in the Dimensionally Stable Portion

According to the present invention, the content of the structural agent is preferably at least 15% by weight, further preferably at least 20% by weight and particularly preferably at least 25% by weight of the total mass of the dimensionally stable portion. But the proportion of the structural agent in the dimensionally stable portion should preferably not exceed a content of 50% by weight, further preferably 40% by weight and particularly preferably 30% by weight.

Suitable structural agents may be inorganic or organic agents. Preferably, the structural agent is selected from at least one natural polymer, at least one synthetic polymer and mixtures thereof.

It is particularly preferable, when the structural agent is capable of swelling in water, thus is capable of increasing its volume by absorption of water and so of providing a diffusion barrier for the active ingredient. Preferable structural agents are characterized by a swelling capacity of higher than 1.5, preferably higher than 3, further preferably higher than 5. It is advantageous, when the structural agent has a swelling capacity of at most 20, preferably at most 15. This means that the volume of the swollen structural agent is preferably not larger than the 20-fold, preferably not larger than the 15-fold of the volume of the non-swollen structural agent. A swelling capacity of the structural agent which is too high may compromise the release of the active ingredient, since this agent is preferably contained in the dosage form in a relatively high proportion. The swelling capacity may be determined by methods which are known by a person skilled in the art, such as for example by microscopic observation of the volume increase during swelling under conditions which are suitable for initiating swelling each.

Preferably, a structural agent which in an aqueous solution in a proportion of 2% by weight at a temperature of 20° C. and a pressure of 101.325 kPa has a viscosity of at least 500 mPas is used. The viscosity is measured by means of a capillary viscometer (DIN 53015). Depending on the desired prolongation of the release of the active ingredient it may be desired also to select higher viscosities. The higher the viscosity of the structural agent, the stronger is the modification of the release. In particularly preferable embodiments under the mentioned conditions the viscosity of the structural agent is even at least 2500 mPas and particularly preferably at least 3500 mPas. But when the viscosity is too high, then possibly the release of the active ingredient may be too slow. This may result in the problem that the active ingredient during its passage through the gastrointestinal tract possibly cannot be released completely or is only released in lower sections of the intestine so that therapeutic plasma levels cannot be achieved. Under the mentioned conditions the viscosity is preferably restricted to at most 200 000 mPas, further preferably to at most 120 000 mPas, still more preferably to at most 90 000 mPas and most preferably to at most 15 000 mPas.

Preferable structural agents have a mean molecular weight (number average molecular weight $M_N$) of at least 5,000, further preferably at least 12,000 and particularly preferably at least 20,000. Structural agents having mean molecular weights which are too low often are not characterized by the required strengths which are necessary for preparing stable and abrasion-resistant dosage forms. On the contrary, structural agents having mean molecular weights which are too high are often characterized by worse solubility so that the release of the active ingredient may be compromised and there is the risk that the active ingredient is only released in deeper sections of the intestine and thus cannot be resorbed sufficiently. The structural agent has preferably a mean molecular weight of at most 250,000, further preferably at most 200,000 and most preferably at most 150,000. A conceivable and preferable structural agent is Methocel E4M having a molecular weight of ca. 100,000.

The structural agent is preferably selected from natural or synthetic polysaccharides, polymethacrylates and their copolymers, polyacrylates and mixtures thereof.

It is particularly preferable, when the structural agent comprises a natural or synthetic polysaccharide. It is particularly preferable, when the structural agent consists of a natural or synthetic polysaccharide. Preferable polysaccharides comprise more than 10 monosaccharide units. Pentoses and hexoses, further preferably selected from glucose, galactose, xylose, fructose, arabinose, mannose, mannuronic acid, guluronic acid, gulose and mixtures thereof, were shown to be suitable monosaccharide units. Particularly preferable natural or synthetic polysaccharides are selected from celluloses, cellulose derivatives, alginates and mixtures thereof.

It is especially preferable, when the structural agent comprises a cellulose derivative. Suitable cellulose derivatives are characterized by average degrees of substitution of at least 1, further preferably at least 1.2 and most preferably at least 1.3. The degree of substitution is the mean number of substituents per glucose unit of the cellulose. When the degree of substitution is too low, then the swelling capacity of the retarding agent and the viscosity may be reduced so that possibly the release of the active ingredient is no longer modified sufficiently.

Preferable cellulose derivatives are selected from methyl cellulose, hydroxypropyl cellulose, hydroxypropylmethyl cellulose and mixtures thereof. Particularly preferable cellulose derivatives are selected from methyl cellulose, hydroxypropylmethyl cellulose and mixtures thereof. A most preferable cellulose derivative is methyl cellulose. It is particularly preferable, when the structural agent in the dimensionally stable portion consists of methyl cellulose.

It is particularly preferable, when the structural agent does not comprise polymers with permanent charge. It is particularly preferable, when the structural agent substantially does not contain ionic substances, in particular no sodium carboxymethyl celluloses. According to the present invention, this means that the structural agent comprises less than 15% by weight, preferably less than 5% by weight and further preferably at most 1% by weight of substances having permanent charge. It is particularly preferable, when in the structural agent no substances with permanent charge are contained. But when substances having permanent charges are contained in the structural agent in too high amounts, then there is the risk that they form precipitates with other substances with permanent charge, such as for example a charged active ingredient. The formation of a precipitate may be disadvantageous for the stability of the dosage form and/or for the release of the active ingredient. Thus it is particularly preferable, when the structural agent and further preferable the dosage form according to the present invention do not contain any sodium carboxymethyl cellulose.

Structural Agents in the Portion Which is Soluble in Gastric Juice

According to the present invention, the content of the structural agent in the portion which is soluble in gastric juice is preferably at least 20% by weight, further preferably at least 25% by weight and particularly preferably at least 30% by weight or at least 45% by weight of the total mass of the portion. But the proportion of the structural agent in the portion which is soluble in gastric juice should preferably not exceed a content of 65% by weight or 55% by weight, further preferably 50% by weight and particularly preferably 40% by weight.

Suitable structural agents may be inorganic or organic agents. Preferably, the structural agent is selected from at least one natural polymer, at least one synthetic polymer and mixtures thereof.

It is particularly preferable, when the structural agent is capable of swelling in water, thus is capable of increasing its volume by absorption of water and so of providing a diffusion barrier for the active ingredient. Preferable structural agents are characterized by a swelling capacity of higher than 1.5, preferably higher than 3, further preferably higher than 5. It is advantageous, when the structural agent has a swelling capacity of at most 20, preferably at most 15. This means that the volume of the swollen structural agent is preferably not larger than the 20-fold, preferably not larger than the 15-fold of the volume of the non-swollen structural agent. A swelling capacity of the structural agent which is too high may compromise the release of the active ingredient, since this agent is preferably contained in the dosage form in a relatively high proportion. The swelling capacity may be determined by methods which are known by a person skilled in the art, such as for example by microscopic observation of the volume increase during swelling under conditions which are suitable for initiating swelling each.

Preferably, a structural agent which in an aqueous solution in a proportion of 2% by weight at a temperature of 20° C. and a pressure of 101.325 kPa has a viscosity of at least 500 mPas is used. The viscosity is measured by means of a capillary viscometer (DIN 53015). Depending on the desired prolongation of the release of the second active ingredient it may be desired also to select higher viscosities. The higher the viscosity of the structural agent, the stronger is the modification of the release. In particularly preferable embodiments under the mentioned conditions the viscosity of the structural agent is even at least 2500 mPas and particularly preferably at least 3500 mPas. But when the viscosity is too high, then possibly the release of the active ingredient may be too slow. This may result in the problem that the active ingredient during its passage through the gastrointestinal tract possibly cannot be released completely or is only released in lower sections of the intestine so that therapeutic plasma levels cannot be achieved. Under the mentioned conditions the viscosity is preferably restricted to at most 200 000 mPas, further preferably to at most 120 000 mPas, still more preferably to at most 90 000 mPas and most preferably to at most 15 000 mPas.

Preferable structural agents have a mean molecular weight (number average molecular weight $M_N$) of at least 5,000, further preferably at least 12,000 and particularly preferably at least 20,000. Structural agents having mean molecular weights which are too low often are not characterized by the required strengths which are necessary for preparing stable and abrasion-resistant dosage forms. On the contrary, structural agents having mean molecular weights which are too high are often characterized by worse solubility so that the release of the active ingredient may be compromised and there is the risk that the active ingredient is only released in deeper sections of the intestine and thus cannot be resorbed sufficiently. The structural agent has preferably a mean molecular weight of at most 250,000, further preferably at most 200,000 and most preferably at most 150,000. A possible structural agent is Vivapur or more exactly Vivapur 101. Degrees of polymerization of these substances may be in a range of 180 to 250, and depending on that, molecular weights may vary and may be in a range of ca. 50,000.

The structural agent is preferably selected from natural or synthetic polysaccharides, polymethacrylates and their copolymers, polyacrylates and mixtures thereof.

It is particularly preferable, when the structural agent comprises a natural or synthetic polysaccharide. It is particularly preferable, when the structural agent consists of a natural or synthetic polysaccharide. Preferable polysaccharides comprise more than 10 monosaccharide units. Pentoses and hexoses, further preferably selected from glucose, galactose, xylose, fructose, arabinose, mannose, mannuronic acid, guluronic acid, gulose and mixtures thereof, were shown to be suitable monosaccharide units. Particularly preferable natural or synthetic polysaccharides are selected from celluloses, cellulose derivatives, alginates and mixtures thereof.

A particularly preferable structural agent in the portion which is soluble in gastric juice is microcrystalline cellulose.

The total proportion of the structural agents in both portions of the dosage form should preferably be at least 15% by weight, further preferably at least 20% by weight, still more preferably at least 22% by weight and particularly preferably at least 25% by weight. When the amount of structural agent used is too low, then the desired effect is not achieved. When the amounts are too high, then the release of the active ingredient is not quick enough and it may be possible that the processability of the dosage form in considerably complicated. Therefore, the proportion of the structural agent in the dosage form should not exceed a value of 55% by weight, further preferably 45% by weight and particularly preferably 35% by weight.

The sum of the proportions by weight of the emulsifier and the structural agent in the dimensionally stable portion should be at least 40% by weight, based on the total mass of the dimensionally stable portion. Both, the emulsifier and also the structural agent support the modification of the release of the active ingredient. Therefore it is preferred that the sum of the proportions is at least 40% by weight so that the release of the active ingredient is optimally modified and plasma peak levels due to a too fast release, in particular in the case of a longer residence time of the dosage form in the stomach, are effectively prevented. In this case, especially the synergistic cooperation of the emulsifier and the structural agent allows an optimum release of the active ingredient together with an optimum processability of the components of the dosage form. As already described above, both, too high proportions of emulsifier and also too high proportions of structural agent in the dosage form are disadvantageous for the processability and the release of the active ingredient. Further preferably, the sum of the proportions by weight of the emulsifier and the retarding agent in the dosage form according to the present invention is at least 45%, still further preferably at least 48% and particularly preferably at least 52%.

In this case it has been shown that a mass ratio of emulsifier to structural agent in the dimensionally stable portion of at least 1:10, preferably at least 1:5 and still more preferably at least 1:2 as well as particularly preferably at least 1:1.2 is advantageous. Preferably, the mass ratio is at most 10:1, further preferably at most 5:1, still further preferably at most 2:1 and particularly preferably at most 1.2:1. In particularly preferable embodiments of the dosage form according to the present invention the mass ratio of emulsifier to structural agent in the dimensionally stable portion is about 1:1.

According to the present invention, the mass ratio of active ingredient to structural agent in the dimensionally stable portion is preferably less than 1:1, further preferably at most 1:1.2, still further preferable at most 1:1.5 and particularly preferably at most 1:1.8. When the proportions of the structural agent in relation to the active ingredient are too low, then the modification of the release of the active ingredient is not very strong. Then there may be the risk that too much active ingredient is already released in the stomach which may result in toxic plasma levels. But the mass ratio should not fall below a value of 1:20, further preferably 1:15, still further preferably of 1:10 and particularly preferably of 1:4. When the proportions of the amount of structural agent are too high, then the release of the active ingredient may be retarded too strong and it may be possible that it is only released in deeper sections of the intestine. Then only insufficient plasma levels are achieved. In addition, the dosage form in total becomes too large and thus the swallowing thereof may become more difficult.

Binders

Binders in the Dimensionally Stable Portion

In the dimensionally stable portion according to the present invention the binder is preferably contained in a content of at least 5% by weight, further preferably at least 10% by weight and particularly preferably at least 30% by weight. Preferably, its content is at most 50% by weight, further preferably at most 40% by weight and particularly preferably at most 35% by weight.

The binders used according to the present invention have the advantage that they very easily can be processed with the other components of the dosage forms according to the present invention and that they, already in low amounts, result in superior performance. In addition, the binders facilitate the processing of the components of the dosage forms according to the present invention and they support the stabilization of the dosage forms in total, preferably they increase the mechanical stability of the dosage forms during their production. For example, the binders are suitable for increasing the melting point of a mixture of the active ingredient and the emulsifier during the production of the dosage forms according to the present invention so that a further treatment of this mixture can easily be conducted.

Suitable binders may be inorganic or organic binders. The binder is preferably a natural or synthetic polysaccharide, comprising two or more identical or different monosaccharide units, in particularly preferably selected from glucose, galactose and mixtures thereof. Such substances are available very cheaply, can be processed very easily and partially at the same time result in a certain decomposing effect. It is particularly advantageous, when the binder at the same time is suitable for masking a bad taste of the active ingredient. Therefore, preferable binders have a sweet taste.

It is particularly preferable, when the binder is selected from calcium phosphate, lactose, starch, starch derivatives and mixtures thereof. From the starches corn starch and pregelatinized starch are particularly preferably due to their simple processability and advantageous properties. It is particularly preferable, when the binder is selected from starch, calcium phosphate and mixtures thereof, wherein it is further preferable, when the binder consists of starch, calcium phosphate or mixtures thereof.

The proportion of this binder in the dosage form should preferably be at least 10% by weight, further preferably at least 15% by weight and particularly preferably at least 20% by weight. Preferably, the proportion of the binder in the dosage form should not exceed a value of 60% by weight, further preferably 55% by weight and particularly preferably 50% by weight. An amount of binder which is too high increases the size of the dosage form and thus is not desired.

Binders in the Portion Which is Soluble in Gastric Juice

Also the portion of the dosage form which is soluble in gastric juice should preferably contain a binder. The proportion of the binder should preferably be at least 30% by weight, further preferably at least 40% by weight and particularly preferably at least 50% by weight. Normally, the binder also promotes the decomposition of the dosage form so that the proportion in the portion which is soluble in gastric juice is preferably higher than the proportion in the dimensionally stable portion. In the context of such a formulation it has been shown that it is advantageous, when in the portion which is soluble in gastric juice the binder is contained in a maximum proportion of 70% by weight, further preferably 65% by weight and particularly preferably 60% by weight.

The binders used according to the present invention have the advantage that they very easily can be processed with the other components of the dosage forms according to the present invention and that they, already in low amounts, result in superior performance. In addition, the binders facilitate the processing of the components of the dosage forms according to the present invention and they support the stabilization of the dosage forms in total, preferably they increase the mechanical stability of the dosage forms during their production. For example, the binders are suitable for increasing the melting point of a mixture of the active ingredient and the emulsifier during the production of the dosage forms according to the present invention so that a further treatment of this mixture can easily be conducted.

Suitable binders may be inorganic or organic binders. The binder is preferably a natural or synthetic polysaccharide, comprising two or more identical or different monosaccharide units, in particularly preferably selected from glucose, galactose and mixtures thereof. Such substances are available very cheaply, can be processed very easily and partially at the same time result in a certain decomposing effect. It is particularly advantageous, when the binder at the same time is suitable for masking a bad taste of the active ingredient. Therefore, preferable binders have a sweet taste.

It is particularly preferable, when the binder is selected from calcium phosphate, lactose, starch, starch derivatives and mixtures thereof. From the starches corn starch and pregelatinized starch are particularly preferably due to their simple processability and advantageous properties. It is particularly preferable, when the binder is selected from starch, calcium phosphate and mixtures thereof, wherein it is further preferable, when the binder consists of starch, calcium phosphate or mixtures thereof.

Further Active Ingredient

The dosage form may contain a further active ingredient, in particular in both, the dimensionally stable portion and also the portion which is soluble in gastric juice. In the treatment of dizziness it was shown that the use of combination preparations is advantageous. In particularly, the solubility of the second active ingredient is considerably different from the solubility of the first active ingredient.

Basically, the processing and the presentation of active ingredients with different solubility properties are problematic. For example, there is the risk that the active ingredient with better solubility is released too fast from the dosage form, while the active ingredient with worse solubility is not released or only insufficiently released. With the dosage form according to the present invention it becomes possible to process active ingredients with different solubility properties, even active ingredients with solubility properties which are considerably different from each other. According to the present invention, solubility properties which are considerably different from each other means that the solubility of the second active ingredient at a pH value of 7 and at 22° C. in an aqueous solution is at least one decimal power higher than the solubility of the first active ingredient at a pH value of 7 and at 22° C. in an aqueous solution. Preferably, the solubility of the second active ingredient at a pH value of 7 and at 22° C. is even higher by a factor of 50 than the solubility of the first active ingredient, especially preferably even higher by a factor of 100, thus two decimal powers. Such active ingredients particularly profit from the formulation according to the present invention, because their processing together with poorly soluble active ingredients in hitherto known dosage forms is problematic.

Preferably, in the dimensionally stable portion the second active ingredient is contained in a proportion of at least 10 mg, further preferably at least 20 mg and particularly preferably at least 30 mg. It is particularly preferable, when it is contained in the dimensionally stable portion in a proportion of at most 100 mg, further preferably at most 80 mg and particularly preferably at most 60 mg. In this way, the proportion of the second active ingredient in the dimensionally stable portion is preferably higher than the proportion of the first active ingredient in this portion. Preferably, the proportion of the second active ingredient in the dimensionally stable portion is higher than the proportion of the second active ingredient in the portion which is soluble in gastric juice.

The proportion of the second active ingredient in the portion which is soluble in gastric juice is preferably at least 10 mg, further preferably at least 15 mg and preferably at most 40 mg, further preferably at most 30 mg. Preferably, the proportion of the second active ingredient in the portion which is soluble in gastric juice is higher than the proportion of the first active ingredient in the portion of the dosage form which is soluble in gastric juice.

Surfactant/Triglyceride

In preferable embodiments the dosage form further contains at least one surfactant. It has been shown that certain surfactants are capable of slowing down the emptying of the stomach and thus the transport of the dimensionally stable portion into the intestine which results in a further prolonged release of the active ingredient(s).

Preferable surfactants are ionic surfactants, in particularly anionic surfactants. It was shown that in this case metallic soaps are particularly advantageous. Preferably, in this case metallic soaps are substances comprising as an anionic component an organic acid and as a cationic component a metal cation. Preferably, the metal cation is selected from alkali metal ions and alkaline earth metal ions. Particularly preferable are alkali metal ions and in particularly sodium and potassium. From the alkaline earth metal ions magnesium and calcium are particularly preferable.

Preferable organic acids which may be present in the surfactants as anionic components are acids with at least 6 carbon atoms. Organic acids with shorter carbon chain lengths have shown to be less effective. But the organic acids should preferably not exceed chain lengths of 22 carbon atoms. In the case of longer carbon chains the synergistic effect in cooperation with the emulsifier is not distinct enough. It is particularly preferable, when the organic acids in the surfactants have chain lengths of at least 10 and at most 18, further preferably at least 12 and at most 16 carbon atoms.

The organic acids may comprise branched or unbranched carbon chains, wherein the carbon chains are preferably unbranched ones. A particularly preferable surfactant is sodium myristate.

The function of the surfactants according to the present invention is to slow down the passage of the chyme through the gastrointestinal tract and thus the resorption of the first active ingredient. Interestingly it was found that this function can in particular be achieved with the metallic soaps described herein. Therefore, the surfactants are preferably a part of the portion which is soluble in gastric juice.

The proportion of the surfactant in the dosage form according to the present invention should preferably be at least 0.5% by weight, more preferably at least 1% by weight or at least 2% by weight, preferably at least 7% by weight, further preferably at least 12% by weight and particularly preferably at least 17% by weight. It has been shown that in this way the effects of the surfactant are particularly distinct. But an amount of preferably 35% by weight, further preferably 25% by weight and particularly preferably 20% by weight should not be exceeded. Otherwise the release of the active ingredient would be compromised too much. The absolute mass of the surfactant in the dosage form should not exceed a value of 300 mg, further preferably 250 mg and particularly preferably 200 mg. Preferably, the minimum amount of the surfactant should not fall below a value of 5 mg or 10 mg, further preferably 50 mg and particularly preferably 100 mg.

The content by mass of the surfactant in relation to the active ingredient should not fall below a proportion of 1:10, preferably 1:5, further preferably 1 to 1, further preferably 1.5 to 1 and particularly preferably 2 to 1. Preferable, this ratio should not exceed a value of 5 to 1, further preferably 4 to 1 and in particularly 3 to 1. When these values are considered, then the above described advantageous effect can be utilized in an optimum manner.

In a preferable embodiment the dosage form of this invention comprises at least one triglyceride. The triglyceride serves for slowing down the gastrointestinal passage of the dosage form. The triglyceride may also be used in combination with the surfactant for further slowing down the release of the active ingredient.

Preferably, the triglyceride comprises a fatty acid residue having at least 10 carbon atoms, further preferably at least 12 carbon atoms and particularly preferably at least 16 carbon atoms. This minimum length of the chain is desirable, because so the prolongation of the residence time of the dosage form in the stomach as part of a dosage form is particularly distinct and so the release of the active ingredient can be supported in a particularly effective manner. But preferably the chain length should not exceed a value of 22 carbon atoms, further preferably 20 carbon atoms. In particularly preferable embodiments all fatty acid residues in the triglyceride fulfill these requirements.

Preferably, the triglyceride may be used in the dosage form according to the present invention in a proportion of at least 10% by weight, further preferably at least 15% by weight and particularly preferably at least 20% by weight. But a maximum proportion of preferably 40% by weight, further preferably 30% by weight and particularly preferably 25% by weight should not be exceeded, since otherwise the release of the active ingredient would be restricted too much.

The absolute mass of the triglyceride in the dosage form should not exceed a value of 500 mg, further preferably 400 mg and particularly preferably 300 mg. The minimum amount of the triglyceride should preferably not fall below a value of 50 mg, further preferably 100 mg and particularly preferably 150 mg.

The content by mass of the triglyceride in relation to the active ingredient should not fall below a proportion of 2 to 1, further preferably 3 to 1 and particularly preferably 3.5 to 1. Preferably, this ratio should not exceed a value of 20 to 1, further preferably 10 to 1 and in particularly 7 to 1. When these values are considered, then the above described advantageous effect can be utilized in an optimum manner.

EXAMPLES

Example 1

Layered Tablet

| Layer 1 | Dimensionally stable portion | |
|---|---|---|
| Content | Component | Function |
| 40.0 mg | dimenhydrinate | second active ingredient |
| 80.0 mg | methyl cellulose | structural agent |
| 40.0 mg | corn starch | binder |
| 80.0 mg | Gelucire 50/13 | emulsifier |
| 20.0 mg | cinnarizine | active ingredient |
| 2.6 mg | Aerosil | flow promotor |
| 5.2 mg | Mg stearate | lubricant |
| 10.4 mg | talcum | releasing agent |
| 278.2 mg | | |

| Layer 2 | Portion which is soluble in gastric juice | |
|---|---|---|
| Content | Component | Function |
| 20.0 mg | dimenhydrinate | second active ingredient |
| 40.0 mg | microcrystalline cellulose | structural agent |
| 25.0 mg | pregelatinized starch | binder |
| 25.2 mg | calcium phosphate | binder |
| 10.0 mg | cinnarizine | active ingredient |
| 0.6 mg | Aerosil | flow promotor |
| 1.0 mg | Mg stearate | lubricant |
| 121.8 mg | | |

For the production of a layered tablet according to the present invention with the above-mentioned composition, at first the dimensionally stable portion is produced. For this purpose the second active ingredient, the structural agent and the binder are mixed. This mixture together with the emulsifier and the active ingredient is heated to 75° C. for conducting melting granulation. After the melting granulation the granules are cooled and screened. These screened granules (preferable grain size 1.0 mm) are mixed with a mixture of the flow promotor, the lubricant and the releasing agent which has also been screened before. The composition obtained in this manner together with the components of the portion which is soluble in gastric juice are compressed. For this purpose the components of the portion which is soluble in gastric juice are mixed and subsequently screened. Here an advantage, namely that the portion which is soluble in gastric juice can be produced very easily, is disclosed. The dosage form prepared in this manner is characterized by an extraordinarily long duration of action, when it is ingested with or after a meal.

Example 2

Coat-Core Tablet

| Core | Dimensionally stable portion | |
|---|---|---|
| Content | Component | Function |
| 20.0 mg | dimenhydrinate | second active ingredient |
| 41.3 mg | microcrystalline cellulose | structural agent |
| 60.0 mg | corn starch | binder |
| 40.0 mg | Gelucire 50/13 | emulsifier |
| 10.0 mg | cinnarizine | active ingredient |
| 1.2 mg | Aerosil | flow promotor |
| 2.5 mg | Mg stearate | lubricant |
| 5.0 mg | talcum | releasing agent |
| 180.0 mg | | |

| Coat | Portion which is soluble in gastric juice | |
|---|---|---|
| Content | Component | Function |
| 40.0 mg | dimenhydrinate | second active ingredient |
| 150.0 mg | microcrystalline cellulose | structural agent |
| 100.0 mg | pregelatinized starch | binder |
| 177.5 mg | calcium phosphate | binder |
| 20.0 mg | cinnarizine | active ingredient |
| 2.5 mg | Aerosil | flow promotor |
| 5.0 mg | Mg stearate | lubricant |
| 5.0 mg | talcum | releasing agent |
| 500.0 mg | | |

The production of a coat-core tablet according to the present invention with the described composition was achieved by mixing the constituents second active ingredient, structural agent and binder. Then the mixture was heated to 75° C. and granulated with a mixture of the active ingredient and the emulsifier. Subsequently, a step of cooling and screening was conducted. The screened granules were mixed with a mixture of the flow promotor, the lubricant and the releasing agent which has also been screened before and formed into tablets. Then these tablets were coated with a film containing an acrylate polymer, a softening agent and talcum. The tablets obtained in such a manner are the core and thus the dimensionally stable portion of this dosage form. For the production of the portion which is soluble in gastric juice, thus here the coat, all constituents of the coat were mixed and pressed onto the coated core.

Figure 1:
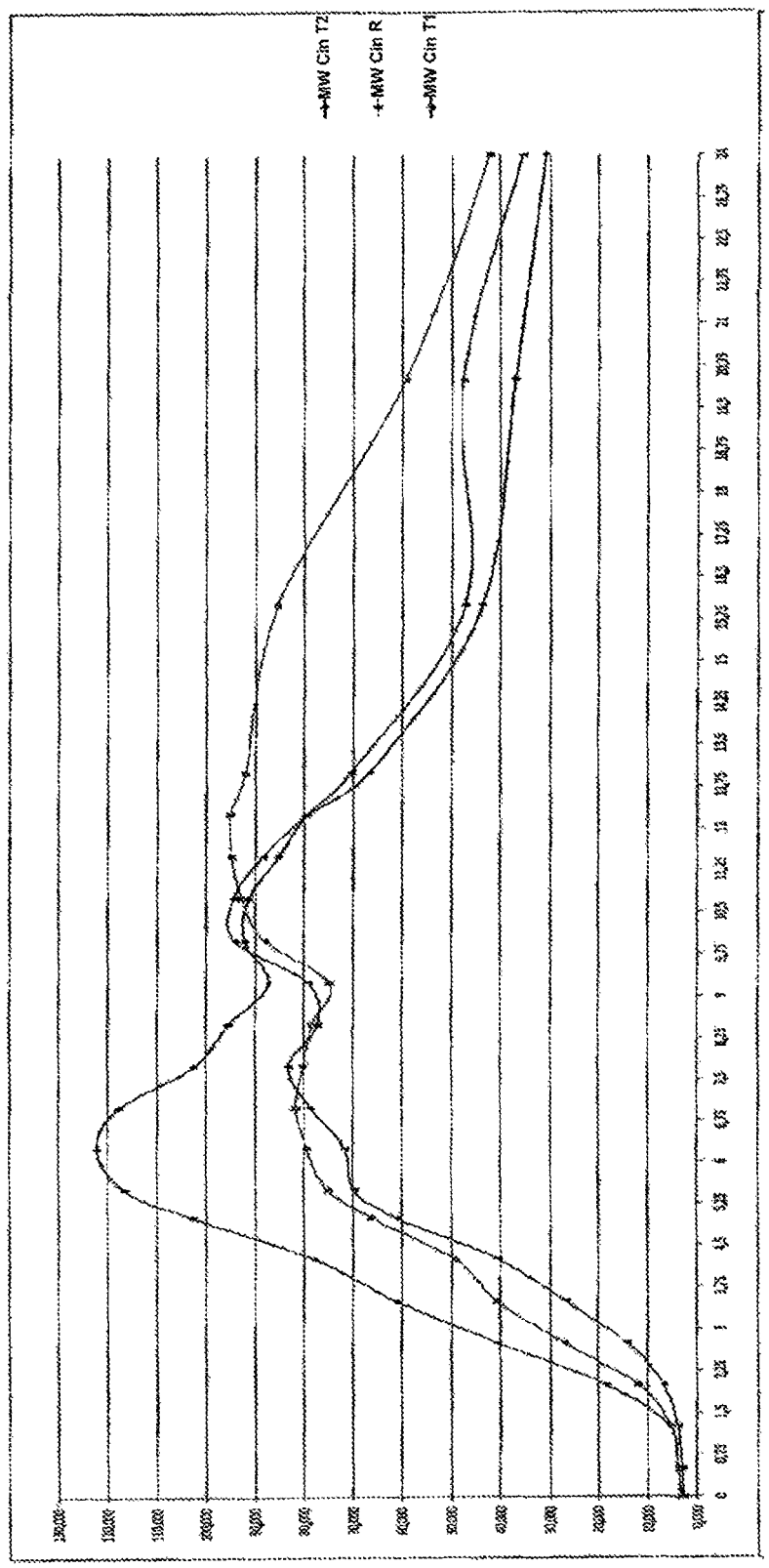
FIG. 1 shows the course of the plasma level (in vivo) of the active ingredient cinnarizine after ingestion of a common dosage form (curve MW Cin R), wherein the active ingredient has been administered after 0 hours, 5 hours and 10 hours. Both other curves MW Cin T1 and MW Cin T2 describe the course of the plasma level for dosage forms according to the present invention. It can be seen very easily that the dosage forms according to the present invention allow a release over a very long period of time.
Figure 2:
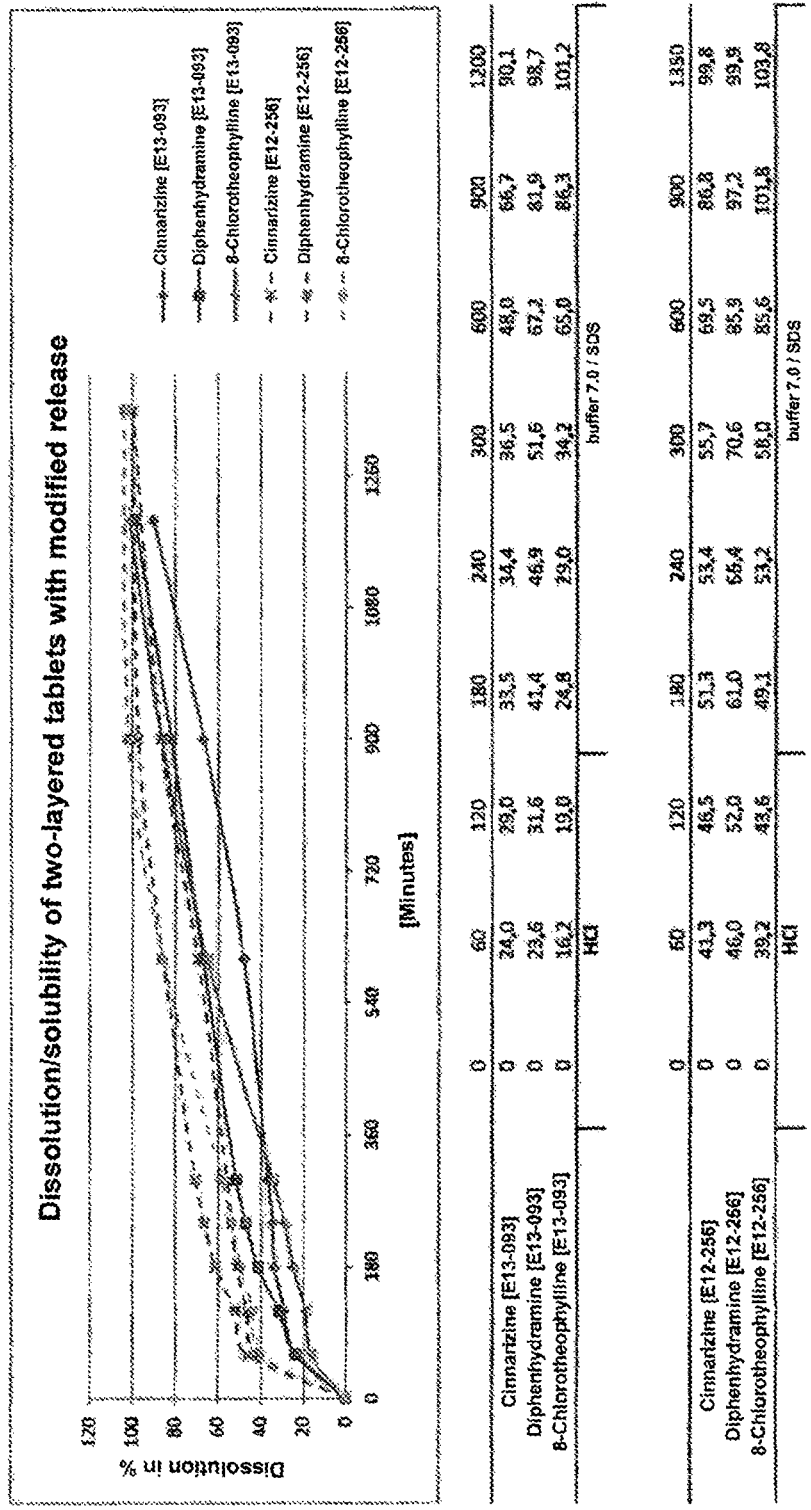
FIG. 2 shows in vitro data for two dosage forms according to the present invention. It relates to the dissolution, i.e. the solubility behavior of two different dosage forms and not only for the active ingredient cinnarizine, but also for diphenhydramine and theophylline. It relates to two embodiments, wherein E12-256 is a preferable embodiment.

The curve MW Cin T2 correlates with the cinnarizine proportion of the dosage form E12-256, while the curve MW Cin T1 correlates with the cinnarizine proportion of the dosage form E13-093.

The invention claimed is:

1. A dosage form comprising
an active ingredient or a derivative, salt and/or prodrug thereof, wherein the active ingredient is cinnarizine, a cinnarizine salt and/or a cinnarizine derivative,
a dimensionally stable portion which does not dissolve in an aqueous medium at a pH value of <5 during a period of time of 2 hours also under stirring and which does not erode under this conditions in an extent that its smallest diameter decreases to a value of <5 mm,
a portion which is soluble in gastric juice which dissolves in an aqueous medium at a pH value of <5 during a period of time of shorter than 2 hours or which erodes under this conditions in an extent that its largest diameter decreases to a value of <2 mm,
wherein both, the dimensionally stable portion and also the portion which is soluble in gastric juice contain a partial amount of the active ingredient,
for use in a method for treating dizziness in humans by administration to a patient with or after a meal at most two times a day.

2. The dosage form according to claim 1, designed as a layered tablet, wherein the dimensionally stable portion and the portion which is soluble in gastric juice each are one layer, or designed as a coat-core tablet, wherein the dimensionally stable portion is the core and the portion which is soluble in gastric juice is the coat.

3. The dosage form according to claim 1, wherein both, the dimensionally stable portion and also the portion which is soluble in gastric juice contain a further active ingredient.

4. The dosage form according to claim 1, wherein the proportion of the active ingredient in the portion which is soluble in gastric juice is about 20% to 65% of the amount of active ingredient in the dimensionally stable portion.

5. The dosage form according to claim 1, wherein the aqueous medium is the phosphate buffer pH 4.5 R of the European Pharmacopoeia 7.0.

6. The dosage form according to claim 1, which is free from antioxidants and/or complexing agents.

7. A method of treating dizziness in humans comprising administering a dosage form to a patient with or after a meal at most two times a day, wherein the dosage form comprises
an active ingredient or a derivative, salt and/or prodrug thereof, wherein the active ingredient is cinnarizine, a cinnarizine salt and/or a cinnarizine derivative,
a dimensionally stable portion which does not dissolve in an aqueous medium at a pH value of <5 during a period of time of 2 hours also under stirring and which does not erode under this conditions in an extent that its smallest diameter decreases to a value of <5 mm,
a portion which is soluble in gastric juice which dissolves in an aqueous medium at a pH value of <5 during a period of time of shorter than 2 hours or which erodes under this conditions in an extent that its largest diameter decreases to a value of <2 mm,
wherein both, the dimensionally stable portion and also the portion which is soluble in gastric juice contain a partial amount of the active ingredient.

8. The method according to claim 7, wherein the administration is conducted one time a day.

9. The method according to claim 7 or 8, wherein the patient is older than 40 years.

10. The method according to claim 9, wherein the patient is older than 50 years.

11. The method according to claim 7, wherein the active ingredient is selected from active ingredients of the active ingredient classes antihistamines, antiemetics, antivertiginous drugs and/or calcium channel blockers.

12. The method according to claim 11, wherein the active ingredient is cinnarizine, in particular in an amount of at least 40 mg, based on the cinnarizine base.

13. The method according to at least one of claim 7, wherein the dosage form is designed as a layered tablet, wherein the dimensionally stable portion and the portion which is soluble in gastric juice each are one layer, or designed as a coat-core tablet, wherein the dimensionally stable portion is the core and the portion which is soluble in gastric juice is the coat.

14. The method according to at least one of claim 7, wherein the administration is conducted within a time frame of up to 1 hour after the ingestion of a meal.

15. The method according to at least one of claim 7, wherein both, the dimensionally stable portion and also the portion which is soluble in gastric juice contain a further active ingredient.

16. The method according to at least one of claim 7, wherein the meal with respect to its composition has the following properties:
a. carbohydrates: >50 g
b. fat: >10 g
c. protein: >10 g.

17. The method according to claim 7, wherein the proportion of the active ingredient in the portion which is soluble in gastric juice is about 20% to 65% of the amount of active ingredient in the dimensionally stable portion.

18. The method according to claim 7, wherein the aqueous medium is the phosphate buffer pH 4.5 R of the European Pharmacopoeia 7.0.

19. The method according to claim 7, which is free from antioxidants and/or complexing agents.

20. The dosage form according to claim 1, wherein the active ingredient has a solubility in an aqueous solution at a pH value of 7 and at a temperature of 22° C. of lower than 0.01 mg/ml.

* * * * *